(12) United States Patent
Milella, Jr. et al.

(10) Patent No.: US 12,408,903 B2
(45) Date of Patent: Sep. 9, 2025

(54) ERGONOMIC MULTI-PART QUICK RELEASE DISPOSABLE BASE FOR MEDICAL INSTRUMENTS

(71) Applicant: ECA Medical Instruments, Inc., Newbury Park, CA (US)

(72) Inventors: Michael J. Milella, Jr., Thousand Oaks, CA (US); Sarah Elizabeth Schaake, Centennial, CO (US)

(73) Assignee: ECA Medical Instruments, Thousand Oaks, CA (US)

( * ) Notice: Subject to any disclaimer, the term of this patent is extended or adjusted under 35 U.S.C. 154(b) by 1244 days.

(21) Appl. No.: 16/968,569

(22) PCT Filed: Feb. 9, 2019

(86) PCT No.: PCT/US2019/017388
§ 371 (c)(1),
(2) Date: Aug. 8, 2020

(87) PCT Pub. No.: WO2019/157403
PCT Pub. Date: Aug. 15, 2019

(65) Prior Publication Data
US 2021/0038206 A1 Feb. 11, 2021

Related U.S. Application Data

(60) Provisional application No. 62/628,888, filed on Feb. 9, 2018.

(51) Int. Cl.
*A61B 17/00* (2006.01)
*B25G 3/18* (2006.01)
*B25G 3/20* (2006.01)

(52) U.S. Cl.
CPC ............... *A61B 17/00* (2013.01); *B25G 3/18* (2013.01); *B25G 3/20* (2013.01); *A61B 2017/0023* (2013.01); *A61B 2017/00424* (2013.01)

(58) Field of Classification Search
CPC ......... B25B 15/00; B25B 15/02; B25B 17/00; B25B 23/0021; B25B 23/0035; B25B 23/0042; B25G 3/00; B25G 3/18; B25G 3/20; A61B 17/00; A61B 2017/0023; A61B 2017/00424
See application file for complete search history.

(56) References Cited

U.S. PATENT DOCUMENTS

| 986,761 A | * | 3/1911 | Roscoe | B23B 31/103 403/301 |
| 1,753,441 A | | 4/1930 | Morehouse | |
| 1,963,462 A | * | 6/1934 | Brock | B25G 3/18 403/328 |

(Continued)

*Primary Examiner* — Robert J Scruggs
(74) *Attorney, Agent, or Firm* — Ferguson Case Orr Paterson LLP

(57) ABSTRACT

The disclosure includes a connection method to connect a shaft to a body. The body and movable latch may be an integral single molded plastic part connected by a flexible hinge, bushing, or a multipart hinge. In operation actuating the movable latch to raise or lower a latching beak within a corresponding open guide in the plastic body. A shaft into a shaft guide in the body which intersects the beak guide to temporarily latching the shaft to the body via a mounting fixture the shaft with the beak; and, wherein the body has a face end and a tail end.

8 Claims, 15 Drawing Sheets

(56) References Cited

U.S. PATENT DOCUMENTS

| | | | |
|---|---|---|---|
| 2,639,158 A | | 5/1953 | Procos |
| 2,682,414 A | * | 6/1954 | Richardson ......... B25B 23/0042 403/325 |
| 4,328,721 A | * | 5/1982 | Massari ................ B25B 15/005 81/439 |
| 4,752,292 A | * | 6/1988 | Lopez ................ A61M 39/1011 604/905 |
| 6,029,549 A | * | 2/2000 | Baker ................. B25B 23/0021 81/439 |
| 7,712,399 B2 | * | 5/2010 | Nenadic ................ B26B 11/003 7/128 |
| 2003/0233913 A1 | | 12/2003 | Hu |
| 2015/0343619 A1 | * | 12/2015 | Lin .................... B25B 23/0035 81/177.1 |

\* cited by examiner

ERGONOMIC MULTI-PART QUICK RELEASE DISPOSABLE BASE FOR MEDICAL INSTRUMENTS

CROSS-REFERENCE TO RELATED APPLICATION

This is a national phase application of International Patent Application No. PCT/US19/17388 filed on Feb. 9, 2019, which claims the benefit of U.S. Provisional Patent Application No. 62/628,888 filed Feb. 9, 2018. The entire contents of each of these applications are incorporated by reference herein.

BACKGROUND

1. Field

This disclosure relates to a plastic disposable mount to withstand forces applied to a shaft supporting a tool.

2. General Background

The medical industry has made use of both reusable and disposable tools and handles. In a surgical context, there is little room for error and the devices must be precise and simple for a surgeon to use during procedures.

Orthopedic surgical procedures can require the creation or enlargement of holes in bones, affixation or removal of fasteners and the like.

Reusable devices require constant recalibration and sterilization to avoid contamination.

DISCLOSURE

The present disclosure provides aspects of ergonomic quick release systems and methods including a plastic molded handle with a front half section and a back half section; the front section comprising; a face end with an interface; a shaft guide collinear with the interface configured to accept a shaft; a beak guide with an open top and an open bottom generally perpendicular to the shaft guide and intersecting the shaft guide; a shaft with a distal end having a mounting fixture and a proximal end configured to mate with the shaft guide; a plastic movable latch with a first guide forming a fluid connection through the movable latch; a threaded second guide formed in the first half section; a bushing configured to separate the movable latch and actuation surface of the first half; a threaded screw configured to be insert through the bushing and connect the first and second guides wherein the plastic movable latch has a first side (107), a second side and a middle region wherein the first side faces the actuation surface and a beak extends therefrom; wherein the beak forms a latch cooperating with the mounting fixture; and, wherein pressing on the movable latch lifts the beak out of the mounting fixture.

Aspects of the movable latch may include an active region on one side of the middle region and the inactive region is on the other side of the middle region and a wherein the beak extends from the inactive region. In some instances depressing the active region raises the inactive region and beak thereby unlatching the shaft. The moving latch may include physical cues on one of the active and inactive region.

In some exemplars the shaft in cross section has at least a portion that is one of square, hexagon; polygon; circular and non-circular. In some instances the shaft has a portion that in cross section is circular with one flat axial region. A portion of the guide may be a fixing guide which cooperates with the flat axial section of prevent an inserted shaft from rotating.

The above exemplars may include a first handle interface formed opposite the face end; a second handle interface formed on the back half; and, wherein the interfaces cooperate to connect the halves.

The present disclosure provides aspects of a connection system and method including a plastic body with a face end; an interface opening at the face end collinear with a shaft guide configured to accept a shaft; a beak guide with an open top and an open bottom generally perpendicular to the shaft guide and intersecting the shaft guide; a plastic hinge portion (integrally formed as part of the body; a plastic movable latch with a first side, a second side and a middle region formed as part of the hinge portion; a beak extending from the latch into the beak guide; and, wherein the beak is configured to a latch a corresponding mount on a shaft. In some instances a shaft with a distal end has a mounting fixture and a proximal end configured to mate with the shaft guide; and, wherein the mounting fixture is configured to cooperate with the beak to mount and unmount the shaft. In some instances an active region is formed on one side of the middle region and the inactive region is on the other side of the middle region; and, wherein the beak extends from the inactive region. The system and method may include depressing the active region raises the inactive region and beak thereby unlatching the shaft. Physical cues on one of the active and inactive region may be added to provide tactile feedback and information regarding operation to a user during operation.

The present disclosure provides aspects of ergonomic quick release systems and methods including a plastic molded handle with a front half section and a back half section; the front section comprising; a face end with an interface; a shaft guide collinear with the interface configured to accept a shaft; a beak guide with an open top and an open bottom generally perpendicular to the shaft guide and intersecting the shaft guide; a shaft with a distal end having a mounting fixture and a proximal end configured to mate with the shaft guide; a plastic movable latch with a tab lock formed therein a flexible integrally molded plastic region extending from an actuation surface of the front section forming a hinge; the hinge terminates in a body tab which is configured to be fixed in the tab lock; wherein the plastic movable latch has a first side, a second side and a middle region; wherein the first side faces the actuation surface and a beak extends therefrom; wherein the beak forms a latch cooperating with the mounting fixture; and, wherein pressing on the movable latch lifts the beak out of the mounting fixture.

Aspects of the movable latch may include an active region on one side of the middle region and the inactive region is on the other side of the middle region and a wherein the beak extends from the inactive region. In some instances depressing the active region raises the inactive region and beak thereby unlatching the shaft. The moving latch may include physical cues on one of the active and inactive region.

In some exemplars the shaft in cross section has at least a portion that is one of square, hexagon; polygon; circular and non-circular. In some instances the shaft has a portion that in cross section is circular with one flat axial region. A portion of the guide may be a fixing guide which cooperates with the flat axial section of prevent an inserted shaft from rotating.

The above exemplars may include a first handle interface formed opposite the face end; a second handle interface formed on the back half; and, wherein the interfaces cooperate to connect the halves. The above exemplars may include a wherein the movable latch is fixed via the tab and tab lock in a neutral position.

The present disclosure provides aspects of ergonomic quick release systems and methods including a plastic molded handle with a front half section and a back half section; the front section comprising, a face end with an interface; a shaft guide collinear with the interface configured to accept a shaft; a beak guide with an open top and an open bottom generally perpendicular to the shaft guide and intersecting the shaft guide; a shaft with a distal end having a mounting fixture and a proximal end configured to mate with the shaft guide; a plastic movable latch with flexible integrally molded plastic region extending therefrom forming a hinge; a latch tab at the top of the hinge; tab lock at the actuation region of the front section and configured to accept and fix the latch tab; wherein the plastic movable latch has a first side, a second side and a middle region; wherein the first side faces the actuation surface and a beak (108) extends therefrom; wherein the beak forms a latch cooperating with the mounting fixture; and, wherein pressing on the movable latch lifts the beak out of the mounting fixture.

Aspects of the movable latch may include an active region on one side of the middle region and the inactive region is on the other side of the middle region and a wherein the beak extends from the inactive region. In some instances depressing the active region raises the inactive region and beak thereby unlatching the shaft. The moving latch may include physical cues on one of the active and inactive region.

In some exemplars the shaft in cross section has at least a portion that is one of square, hexagon; polygon; circular and non-circular. In some instances the shaft has a portion that in cross section is circular with one flat axial region. A portion of the guide may be a fixing guide which cooperates with the flat axial section of prevent an inserted shaft from rotating.

The above exemplars may include a first handle interface formed opposite the face end; a second handle interface formed on the back half; and, wherein the interfaces cooperate to connect the halves. The above exemplars may include a wherein the movable latch is fixed via the latch tab and tab lock in a neutral position.

The general description and the following detailed description are exemplary and explanatory only and are not restrictive of the disclosure, as defined in the appended claims. Other aspects of the present disclosure will be apparent to those skilled in the art in view of the detailed description of the disclosure as provided herein.

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale.

DRAWINGS

FURTHER DISCLOSURE

Figure 1:
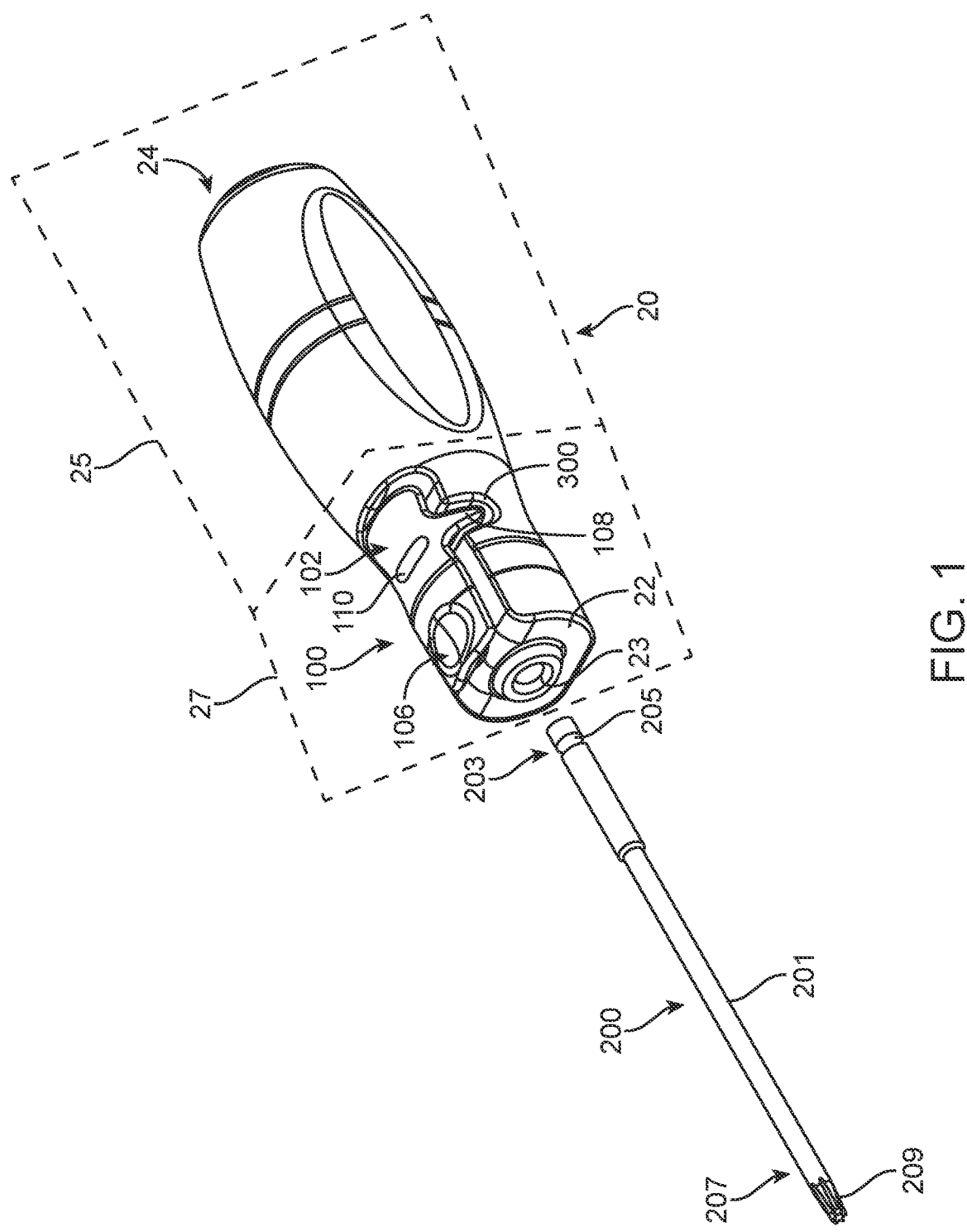
FIG. 1 is a perspective view of aspects of an ergonomic disposable quick release device and system.
Figure 2:
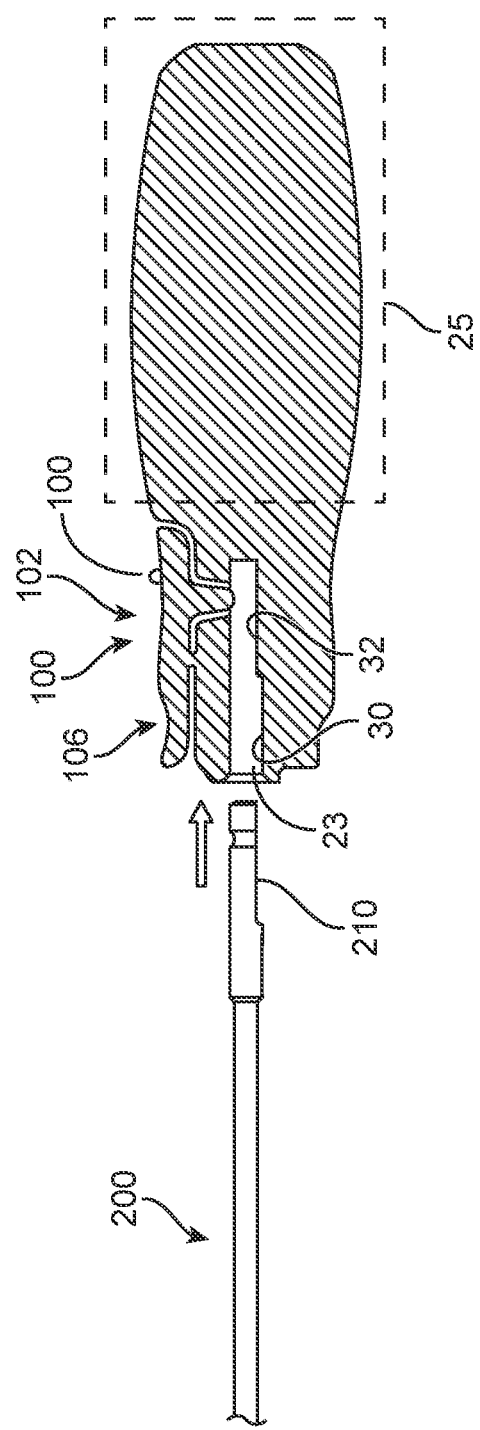
FIG. 2 is a cutaway view of the system of FIG. 1.
Figure 3:
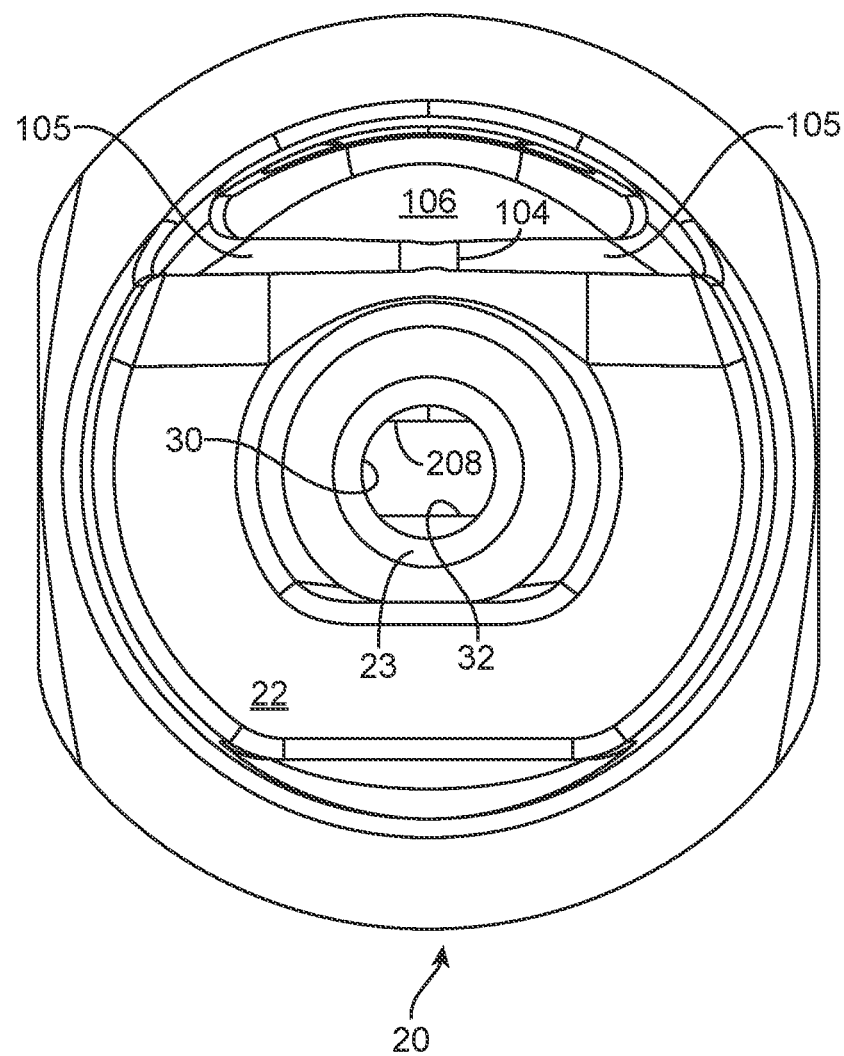
FIG. 3 is a front view of the handle and tool mount shown in FIG. 1.

Referring to FIG. 1 shows an exterior perspective view of an exemplar of a disposable quick release system with a tool unmounted. FIGS. 4A, 4B and 7-10 show exterior views of a disposable quick release system with tool mounted.

FIGS. 1-12 illustrate some aspects of exemplary implementations of ergonomic disposable quick release systems and devices.

Disposable tools in a surgical or other medical environments provide single use calibrated devices which require no sterilization or maintenance. While disposable plastic molded devices would not withstand all the harsh rigors of multiple sterilizations, and remain calibrated for hundreds or thousands of uses, they do provide light-weight alternatives. The single piece hinge and lever shown in aspects of the disclosure would be either cost prohibitive or simply not possible if constructed of metal substrates or other materials which can withstand the rigors of reuse, cleaning and sterilization.

FIG. 1 shows an unmounted system 10. The system includes a plastic molded body or handle 20 and a shaft 200. The shaft has a generally elongated body 201 with a distal end 203 having a mounting fixture 205. At the proximal end 207 of the body 201 is a work piece engaging tip 209. The tip may be a tool such as a resector, screw driver, socket or grabbing, other fastening or cutting end. The engaging tip may also be a separate piece (not shown) which mates with the proximal end 207 (not shown).

Figure 11:
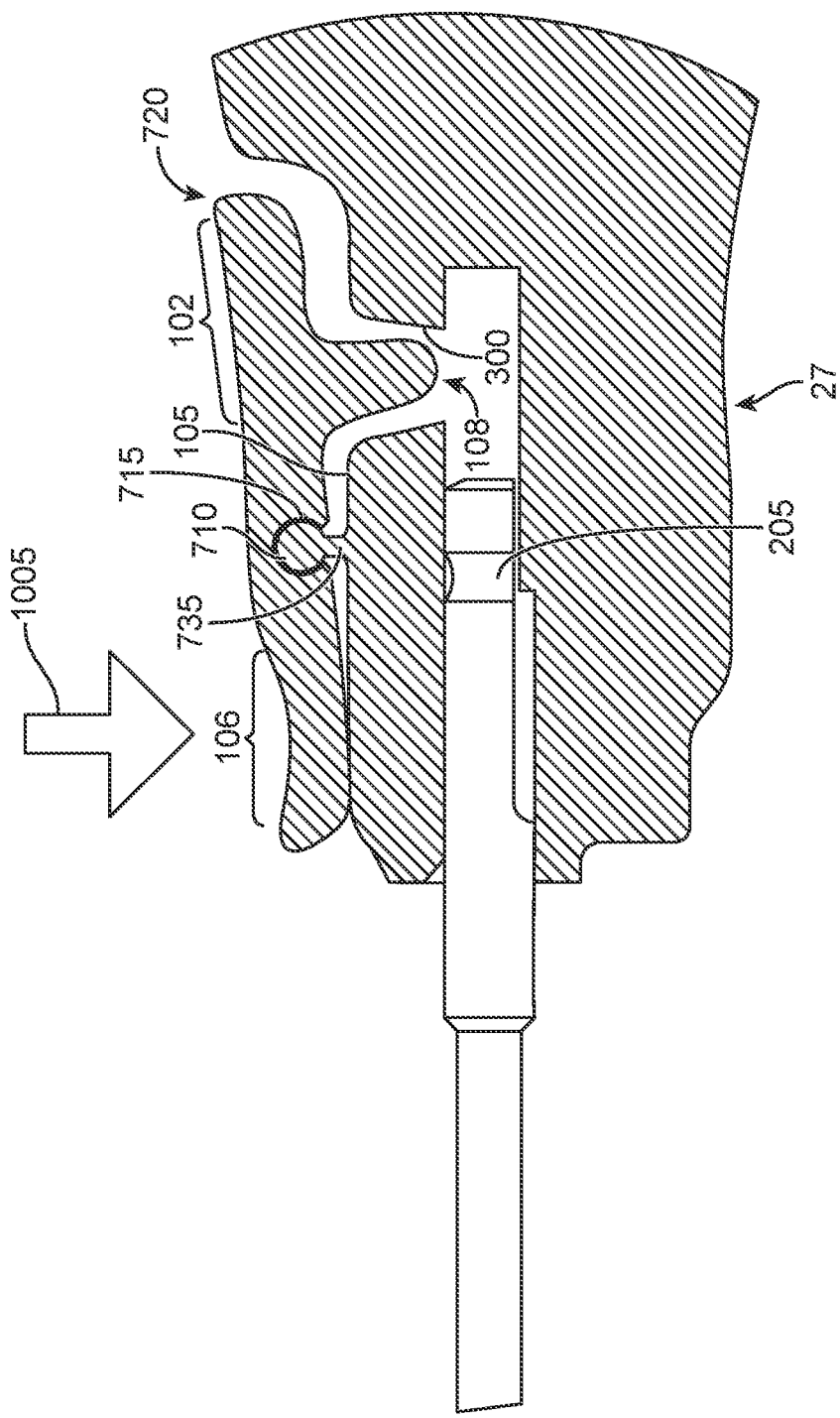
FIG. 11 shows a multipart ergonomic disposable quick release device and system with tool inserted but unmounted.

The body 20 has a face end 22 with a shaft mounting interface 23 therein and distal tail end 24. The handle 20 may be unitary or divided into two or more segments or portions. A back half 25 for gripping and to rotate or otherwise move to impart force to the tip 207. The handle may be configured into a plethora of shapes. A front half 27 wherein the mounting and release of the tool and shaft occurs. Those of ordinary skill in the art will recognize that included within the disclosure is cylindrical, "T" shaped, polygonal or other designs. It is also within the disclosure as shown in FIG. 11 that the front half 27 may have a first handle interface 27' which is a latch/catch which connects with a second handle interface 25' also part of a latch/catch on the back half. The interfaces may be cooperating threads, latch/catch, bonded, glued or welded, co-molded or otherwise bonded together. These arrangements allow for a single front half with fixation mechanisms to be leveraged and used with a variety of back halves. The front half and back half may be formed of dis-similar materials.

Formed as part of the front half 27 of the handle body is a flat region 28 to provide a physical indication of orientation. Also formed as part of the front half is the integrated movable latch 100. The latch is formed of the same material as the handle at the same time preferably via injection molding. The integrated latch 100 may be further divided into four portions, an inactive region 102 which can be grabbed by a user but will not act to release a shaft 200. A pivot or hinge portion 104 which is integrally formed as part of the handle. The hinge is a thin region of plastic configured to flex when an active region 106 is depressed. The hinge region is a single region of plastic that flexes due to its size and position thereby allowing the latch to raise or lower on either side of it. The hinge spans from the actuation surface 105 directly below the lever to the lever. By depressing the active region 106 a latching beak 108 is lifted from a beak guide 300 whereby the distal end 203 of the shaft may be removed.

The hinge portion, in some exemplars, is sufficient to degrade with usage. In particular because the device is disposable a failure of the hinge will disabuse a user of attempting to reuse the device. In other instance the plastic materials selected to form the hinge are such that they become more brittle and/or have reduced memory when subjected to traditional sterilization methods. In yet other instances the hinge region is frangible ad will fail at a predetermined amount of actuations.

Physical cues 110 such as raised ribs may be added to either the inactive region 102 (or conversely the active region 106) to allow a user to feel the area of the lever to depress or identify the area of the lever to avoid.

In operation the latching beak 108 moves generally linearly within the beak guide 300 and functions to reversibly mate with the mounting fixture 205 at the distal end 203 of the shaft. To mount a shaft the distal end 203 is inserted into the mounting interface 23 and then into the shaft guide 30. The distal end 203 reaches the beak 108 and when adequate force is applied the distal end can displace the beak 108 upward allowing the shaft to pass until the mounting fixture 205 catches the beak 108. The active region 106 of the lever is positioned towards the proximal end of the handle. Depressing the active region 106 raises the beak 208 and can be used to insert or withdrawal a shaft. By placing the active region 106 in front of the hinge portion 104 a user is less likely to accidentally release a shaft when grasping the handle. The physical cues 110 although optional also provide a user an indication of where the inactive region of the lever is to avoid unintentional release of shaft.

The shape of the shaft guide 30 is configured to accept shafts with a corresponding shape. Some shafts have a circular cross section with one flat axial segment, other shafts may be polygonal in cross section. FIGS. 2, 3, 5A-6 show a shaft guide 30 configured to accept a shaft with a flat axial section. The guide 30 tapers to a fixing guide 32 which has a flat section corresponding to the flat axial section 210 of the shaft. The fixing guide 32 inhibits rotation of a mounted shaft within the handle. Those of ordinary skill in the art will recognize that a polygonal shaft would fit into a guide that was configured to accept a polygonal cross sectional shaft and such a configuration is within the scope of this disclosure. The flat region 28 is formed as an alignment guide whereby a user will have a physical cue that is parallel with the fixing guide within the front section. Accordingly, a shaft with a flat region may be more easily aligned with the fixing guide.

Figure 5A:
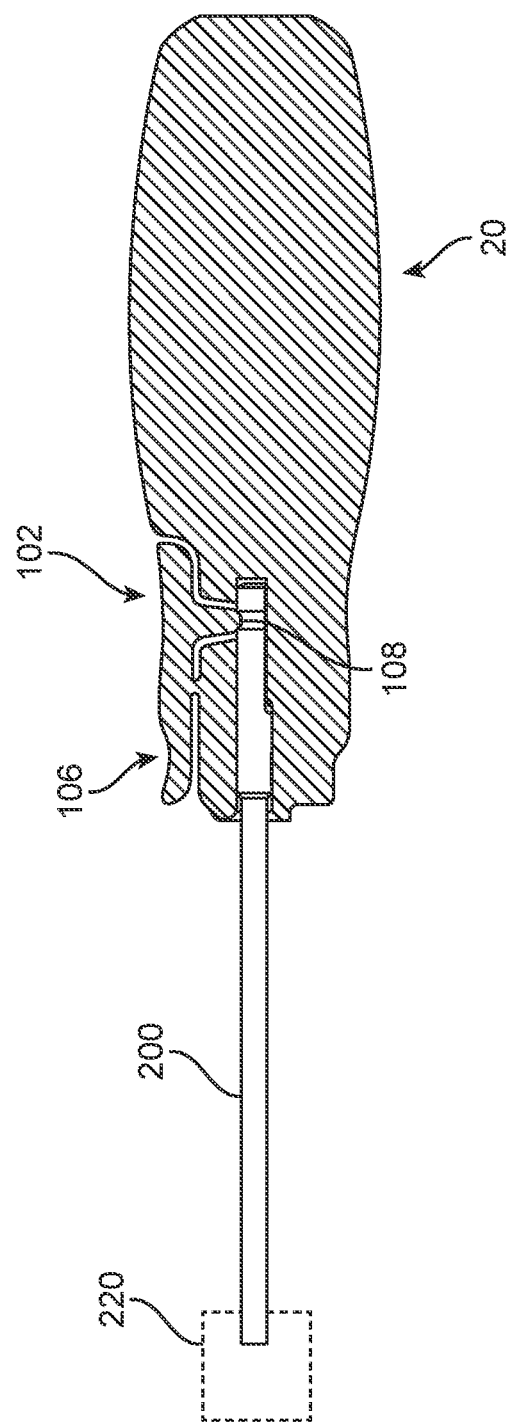
FIGS. 5A-5C are cut-away views of an ergonomic disposable quick release device and system with tool fitted fully into the guide.
Figure 5B:
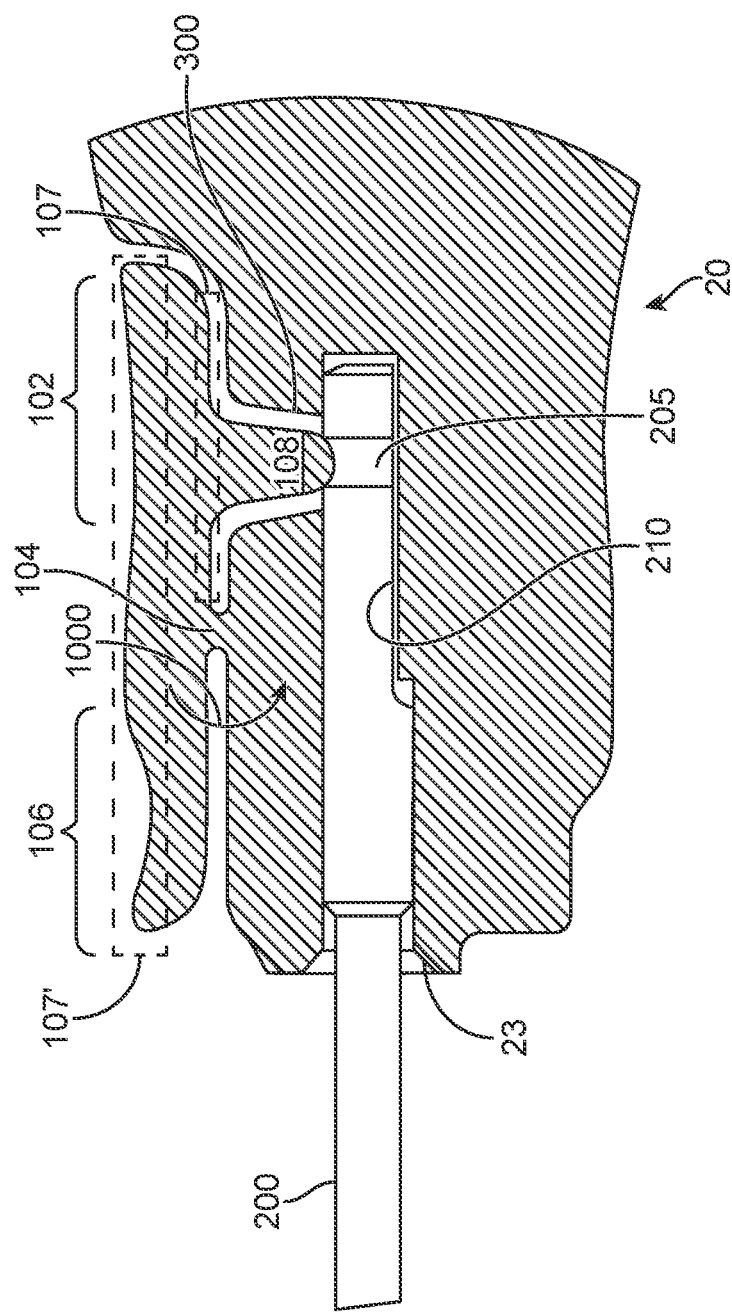
Figure 5C:
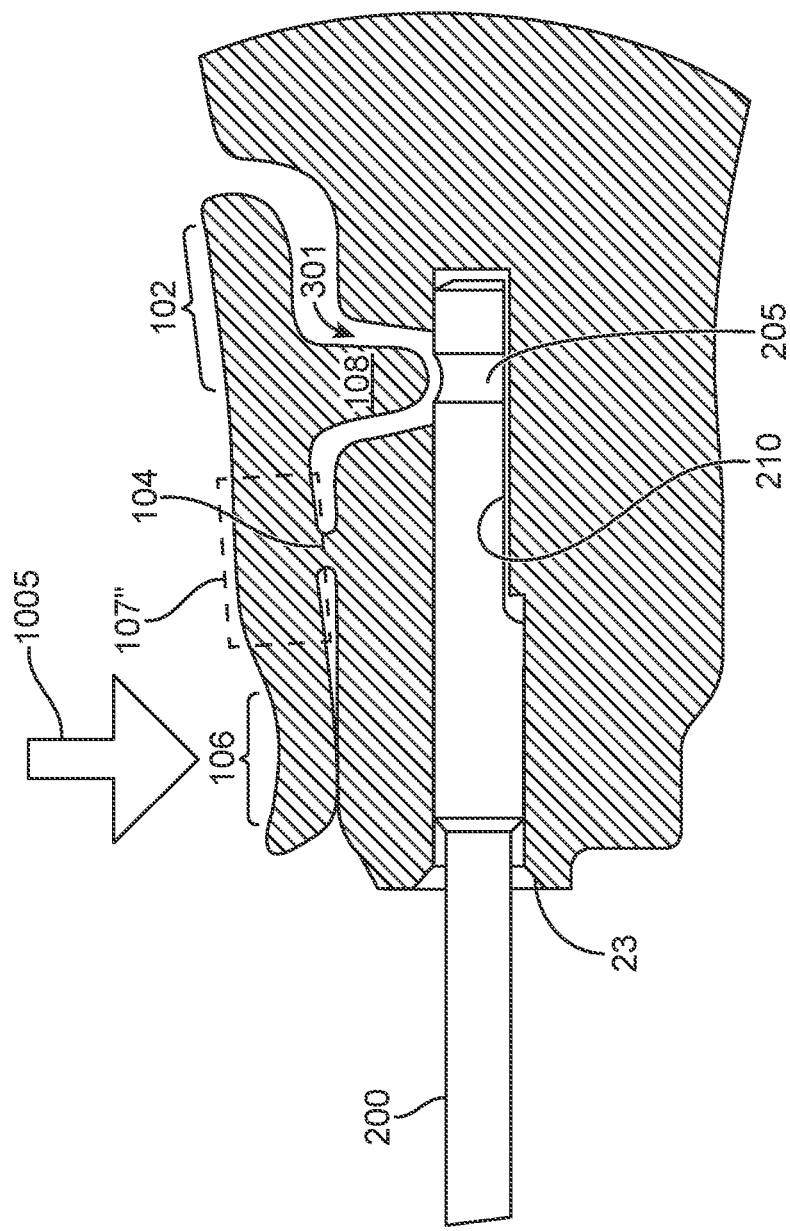

FIG. 5B shows a cut-away close-up of the exemplar shown in FIG. 5A. The movable latch 100 articulates vis a vie the hinge portion 104. Applying pressure to the active region 106 causes the movable latch 100 to rotate about the hinge 104 along the line of arrow 1000 thereby raising the beak 108 from the mounting fixture 205 of the shaft. The beak 108 extends from the first side 107 of the movable latch into a beak guide 300 and connecting with the mounting fixture whereby its movement out of the mounting fixture releases the shaft for removal and/or replacement. FIG. 5C shows the unlatching of the shaft when pressure is applied along the line of arrow 1005 to the active region 106. The active and inactive regions are formed on the second side 107' of the latch. The latch connects to the hinge portion 104 at its middle section 107".

Figure 6:
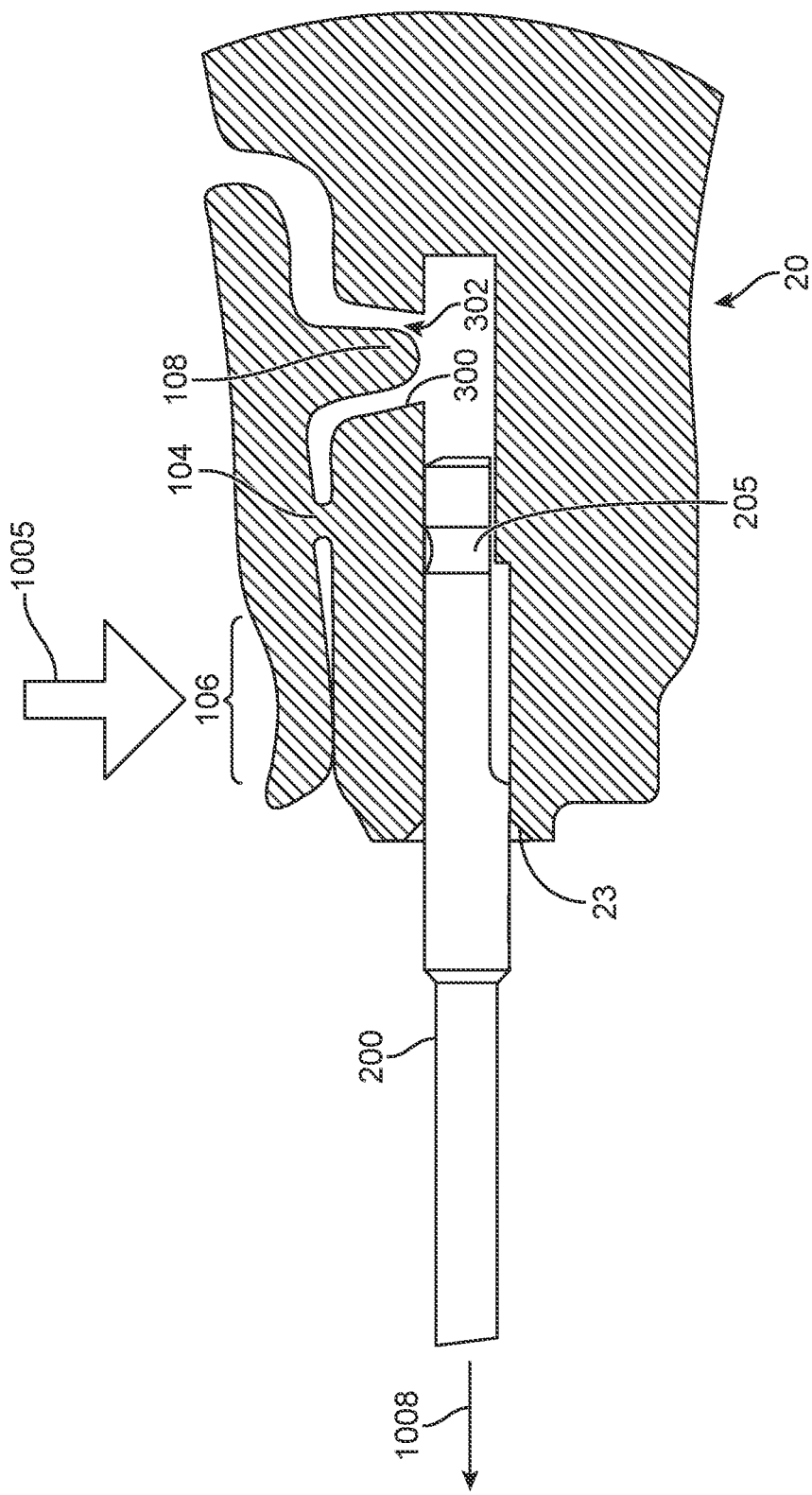
FIG. 6 is a cut-away view of an ergonomic disposable quick release device and system showing tool mount engagement/disengagement.

FIG. 6 shows aspects of a disposable quick release system wherein the shaft 200 is within the shaft guide 30 but not latched via the beak and mounting fixture 205. The beak is raised within the beak guide 300 via force applied to the active region 106 of the movable latch 100. To fix the shaft the user further inserts the shaft into the guide along the line of arrow 1008 until the beak 108 and mounting fixture are connected. To withdraw the shaft the force is applied to the active region 106 to raise the beak 108. The inactive region is illustrated in this exemplary with raised physical cues to provide feedback to the user regarding what portion of the movable latch he/she is in contact with.

Figure 4A:
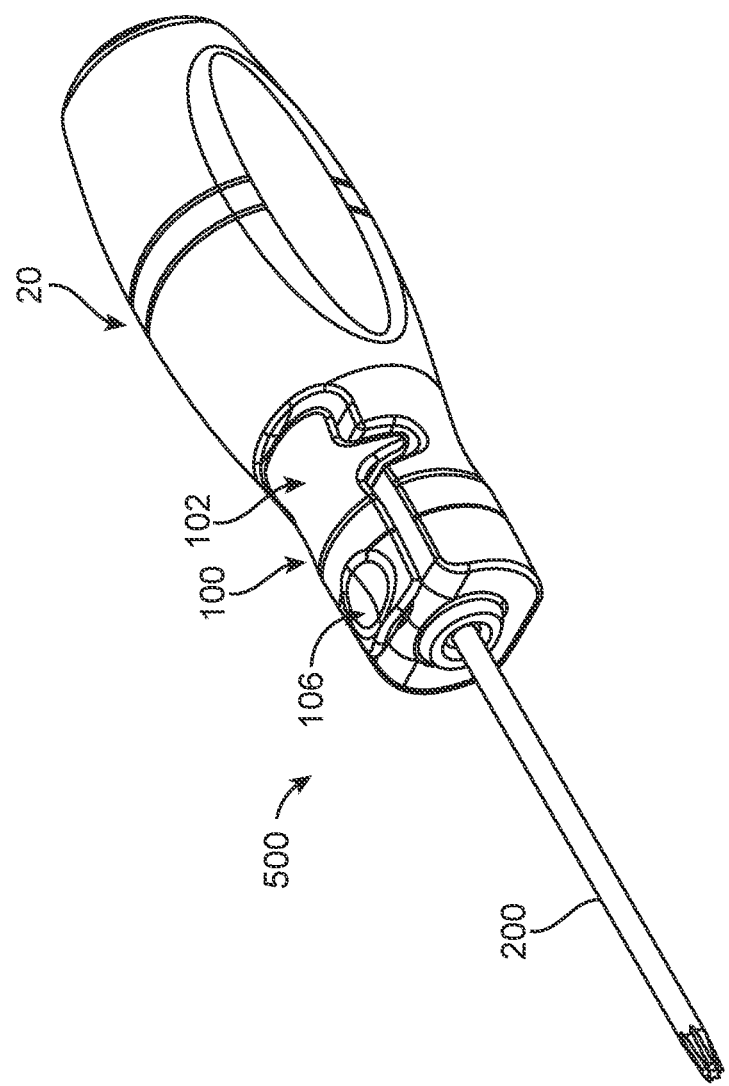
FIGS. 4A and 4B are front and rear perspective views of an ergonomic disposable quick release device and system.
Figure 4B:
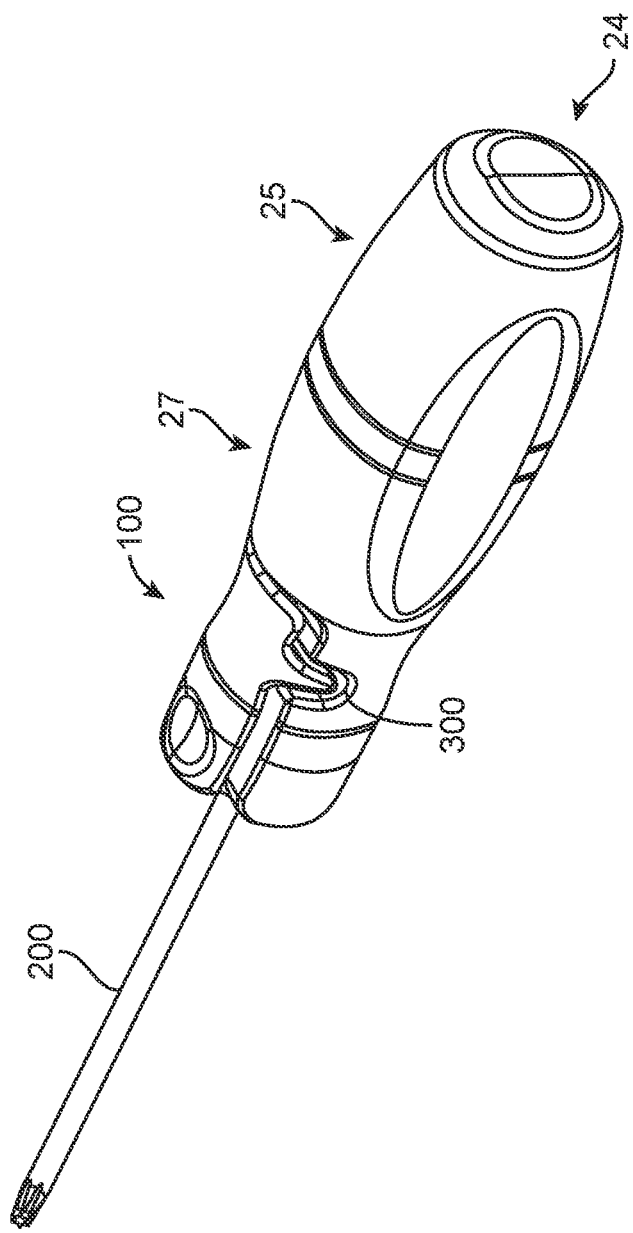

FIGS. 4A and 4B show two perspective views of the disposable quick release device 500. FIGS. 7 through 10 show top, front, back, bottom and side views of aspects of disposable quick release devices and systems. The tool 220 affixed at the proximal end 207 of the shaft 200 is shown as a block to indicate it may be a blade, socket, or the like. Those of ordinary skill in the art will recognize that a variety of tools may be connected to or formed integral to the shaft. The block also denotes a mounting interface to connect said tool(s).

Figure 7:
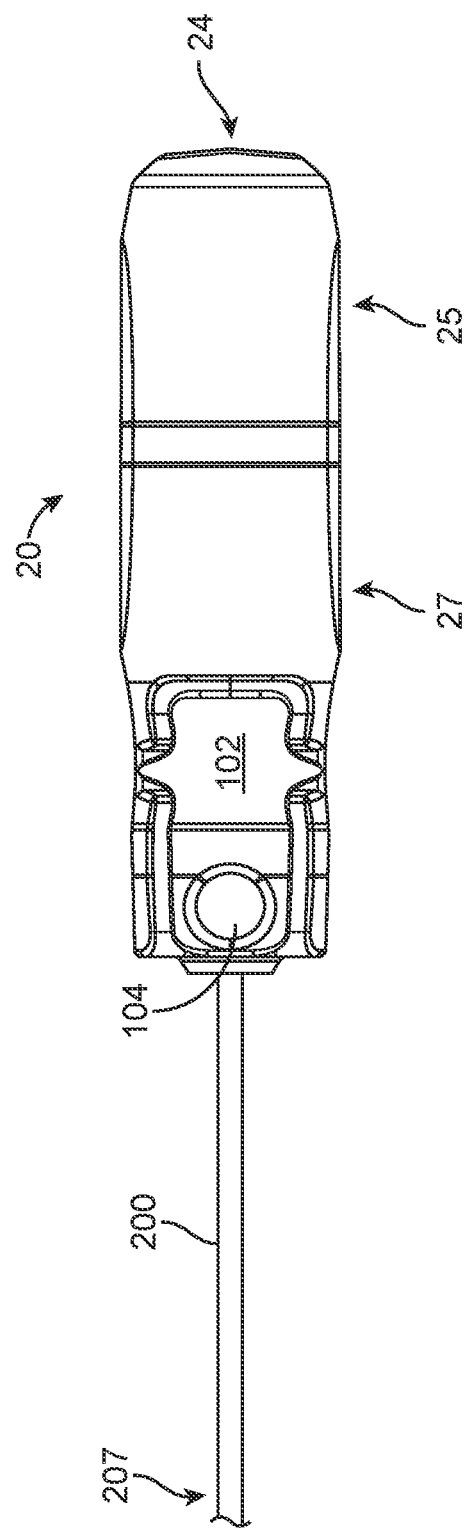
FIG. 7 is a top view of an ergonomic disposable quick release device and system with tool mount
Figure 8:
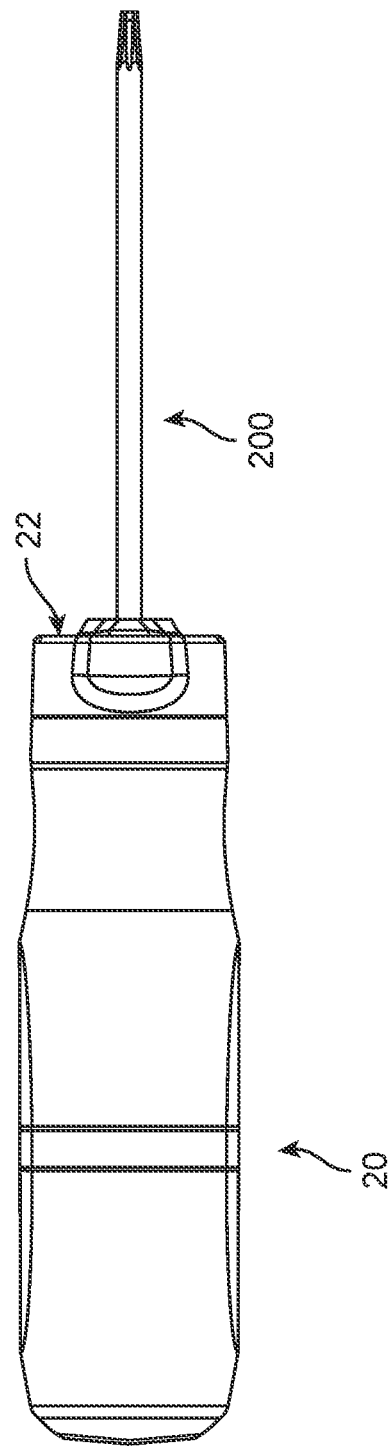
FIG. 8 is a bottom view of an ergonomic disposable quick release device and system with tool mounted.
Figure 9:
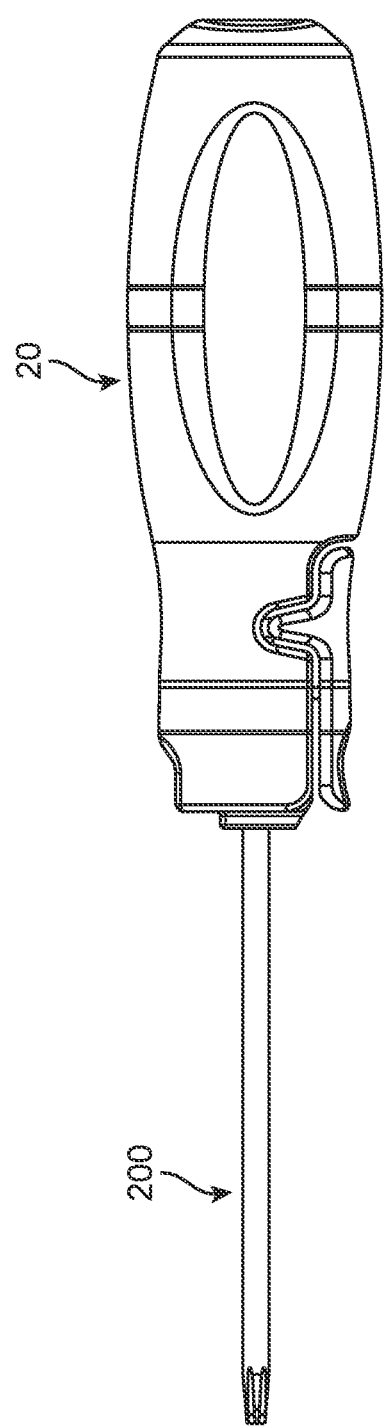
FIG. 9 is a side view of an ergonomic disposable quick release device and system with tool mounted.

FIGS. 7-9 show various external views of disposable quick release devices.

Figure 10:
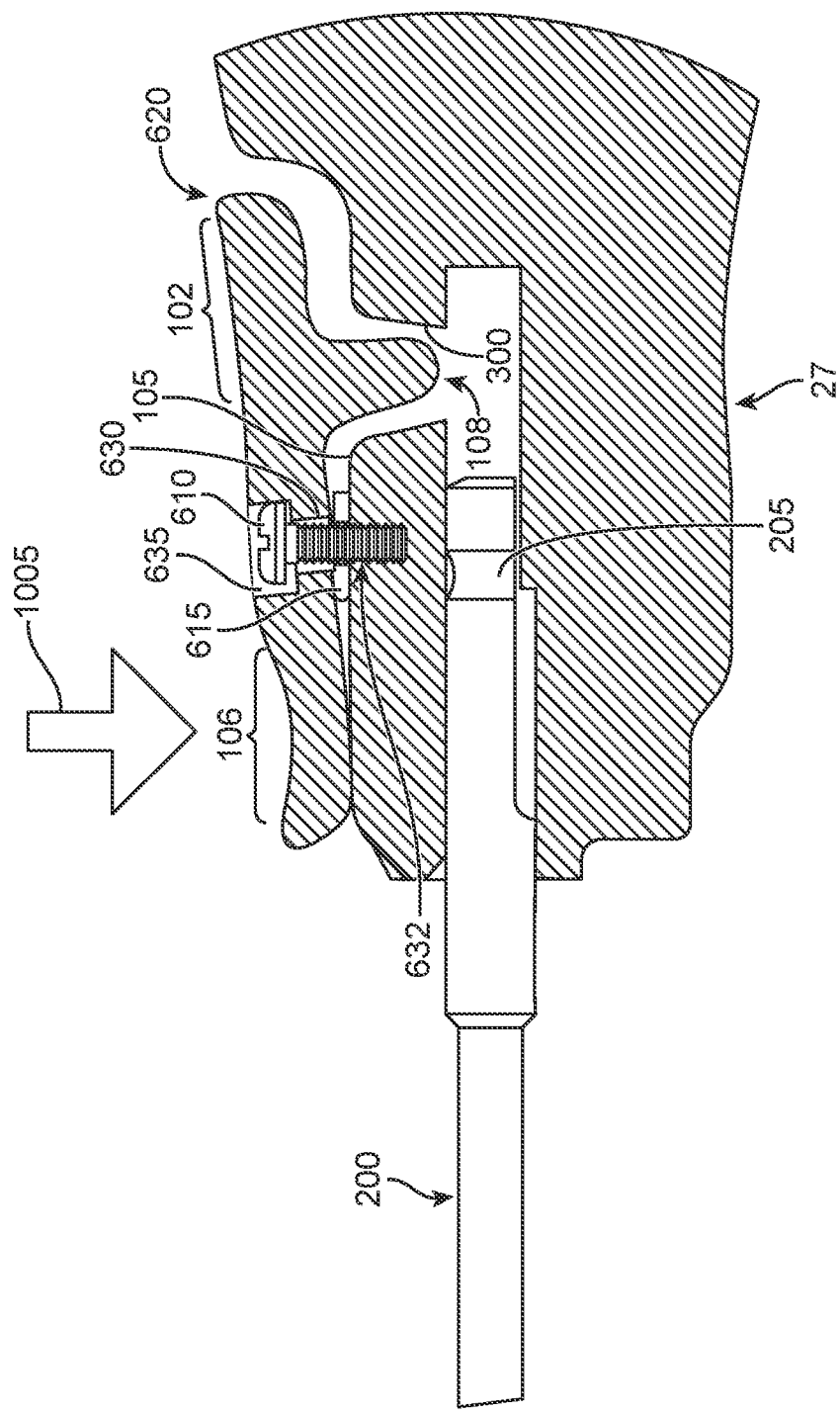
FIG. 10 shows a multipart ergonomic disposable quick release device and system with tool inserted but unmounted.
Figure 12:
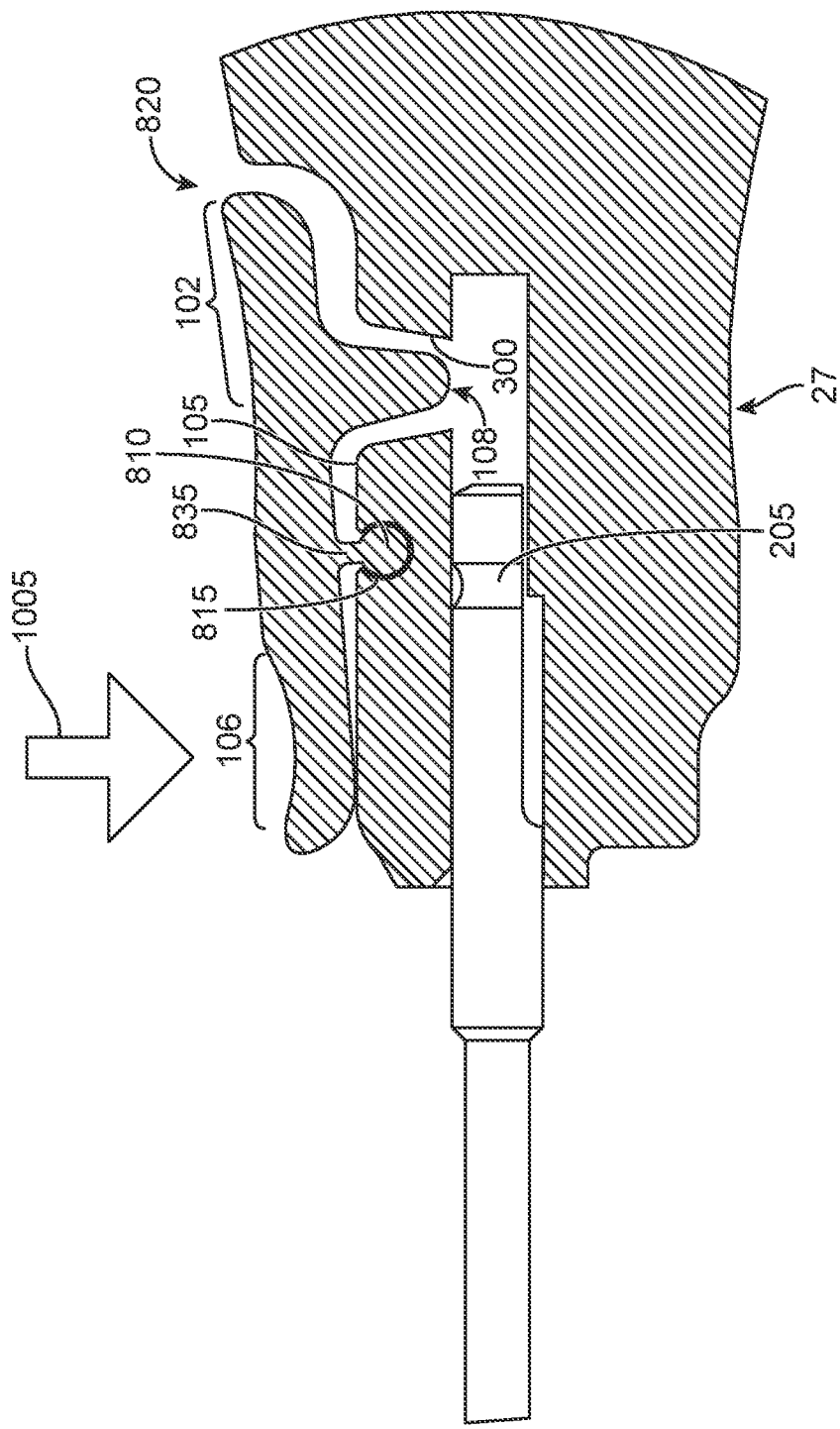
FIG. 12 shows a multipart ergonomic disposable quick release device and system with tool inserted but unmounted.

FIGS. 10-12 show partially cut-away views of several exemplars. Each of those figures shows a portion of the font half 27 and aspects of latching device handles and systems with multi-part handle/latch configurations.

FIG. 10 shows a cut-away close-up of an exemplar configured with a screw 610 and bushing 615 working cooperatively to attach movable latch 620 to the front half 27. The movable latch 620 is mounted, movably, to the front half 25 above the actuation region 105 above the busing. The bushing is positioned between the movable latch and the actuation region 105 aligned with a first guide 630 forming a fluid connection through the movable latch and a second guide 632 forming a mating guide or channel in the first half; both are configured to accept the threaded screw 610. A counter sunk top portion of the guide 635 may be provided. Those of ordinary skill in the art will recognize that the screw and threaded guide may be replaced with a post and a friction fit or a post and adhesive or sonic weld to fix the movable latch in a neutral position above the actuation region. A neutral position means that the latch is fixed so that the beak 108 in the guide 300 extends to a point that would catch the mounting fixture 205 when the shaft is fully inserted into the front half 27. To actuate movable latch 620 pressure is applied to the active region 106 along the line of arrow 1005 which causes the movable latch 620 to compress the bushing 615 and rotate about the screw 610, thereby raising the beak 108. The beak 108 extends from the first side 107 of the movable latch into a beak guide 300 and connecting with the mounting fixture whereby its movement out of the mounting fixture releases the shaft for removal and/or replacement.

FIG. 11 shows a cut-away close-up of an exemplar configured with a body tab 710 and corresponding tab lock 715 which work cooperatively to attach movable latch 720 to the front half 27. The movable latch 720 is mounted, movably, to the body tab 710. The body tab 710 is formed at one end of the hinge 735 which is an integral portion of the front half 27 above the actuation region 105. The hinge 735 is a flexible extended region of the front half 27. The body tab 710 is fixed rigidly into the tab lock 715. The tab lock is a cavity with an opening to accept the corresponding tab. The movable latch is fixed to the body tab 710 in a neutral position above the actuation region. A neutral position means that the latch is fixed so that the beak 108 in the guide 300 extends to a point that would catch the mounting fixture 205 when the shaft is folly inserted into the front half 27. To actuate movable latch 720 pressure is applied to the active region 106 which causes the movable latch 720 to deform/bend the hinge 735 and rotate the movable latch about the hinge thereby raising the beak 108. The beak 108 extends from the first side 107 of the movable latch into a beak guide 300 and connects with the mounting fixture whereby its movement out of the mounting fixture releases the shaft for removal and/or replacement.

FIG. 12 shows a cut-away close-up of an exemplar configured with a movable latch tab 810 and corresponding tab lock 815 which work cooperatively to attach movable latch 820 to the front half 27. The movable latch 820 is mounted, movably, to the movable latch tab 810. The movable latch tab 810 is formed at one end of the hinge 835 which is an integral portion of the movable latch. The movable latch tab 810 is fixed into the tab lock 815 at the actuation region 105. The tab lock is a cavity with an opening to accept the corresponding movable latch tab. The hinge 835 is a flexible extended region of the front half 27. The movable latch tab lock 810 is fixed rigidly into the tab lock 815. The movable latch is fixed in a neutral position above the actuation region. A neutral position means that the latch is fixed so that the beak 108 in the guide 300 extends to a point that would catch the mounting fixture 205 when the shaft is fully inserted into the front half 27. To actuate movable latch 820 pressure is applied to the active region 106 which causes the movable latch 820 to deform/bend the hinge 835 and rotate the movable latch about the hinge thereby raising the beak 108. The beak 108 extends from the first side 107 of the movable latch into a beak guide 300 and connects with the mounting fixture whereby its movement out of the mounting fixture releases the shaft for removal and/or replacement.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An ergonomic quick release system comprising:
    a plastic molded handle with a front half section and a back half section
    the front section comprising:
        a face end with an interface comprising:
            a shaft guide collinear with the interface configured to accept a shaft; and
            a fixing guide distal to said shaft guide and having a flat section connected to and raised above said shaft guide, wherein said fixing guide has a smaller inner diameter relative to said shaft guide;
        a beak guide with an open top and an open bottom generally perpendicular to the shaft guide and intersecting the interface;
        said shaft having a distal end having a flat section configured to mate with said flat section on said fixing guide and having a mounting fixture;
        a plastic movable latch with a tab lock formed therein; and
        a flexible integrally molded plastic region extending from an actuation surface of the front section forming a hinge;
    wherein the hinge terminates in a body tab which is configured to be fixed in the tab lock,
    wherein the plastic movable latch has a first side, a second side and a middle region;
    wherein the first side faces the actuation surface and a beak extends therefrom; wherein the beak forms a latch cooperating with the mounting fixture; and
    wherein pressing on the movable latch lifts the beak out of the mounting fixture.

2. The system of claim 1 further comprising:
    an active region on one side of the middle region and an inactive region on the other side of the middle region; and,
    wherein the beak extends from the inactive region.

3. The system of claim 2 wherein depressing the active region compresses a portion of a bushing and raises the inactive region and beak thereby unlatching the shaft.

4. The system of claim 2 further comprising raised ribs on one of the active and inactive region.

5. The system of claim 1 wherein the movable latch is fixed via said body tab and said tab lock in a neutral position.

6. An ergonomic quick release system comprising:
    a plastic molded handle with a front half section having an actuation region and a back half section;
    the front section comprising:
        a face end with an interface comprising:
            a shaft guide collinear with the interface configured to accept a shaft; and
            a fixing guide distal to said shaft guide and having a flat section connected to and raised above said shaft guide, wherein said fixing guide has a smaller inner diameter relative to said shaft guide;
        a beak guide with an open top and an open bottom generally perpendicular to the shaft guide and intersecting the interface;
        said shaft having a distal end having a flat section configured to mate with said flat section on said shaft guide and having a mounting fixture and;
        a plastic movable latch with flexible integrally molded plastic region extending therefrom forming a hinge having a bottom;
        a latch tab at the said bottom of said hinge; and
        a tab lock at the actuation region of the front section and configured to accept and fix the latch tab;
    wherein the plastic movable latch has a first side, a second side and a middle region;
    wherein the first side faces the actuation region and a beak extends therefrom; wherein the beak forms a latch cooperating with the mounting fixture; and
    wherein pressing on the movable latch lifts the beak out of the mounting fixture.

7. The system of claim 6 further comprising:
    an active region on one side of the middle region and an inactive region on the other side of the middle region; and,
    wherein the beak extends from the inactive region.

8. The system of claim 7 further comprising physical cues on one of the active and inactive region.

* * * * *